(12) United States Patent
Madjarov

(10) Patent No.: US 10,524,943 B2
(45) Date of Patent: Jan. 7, 2020

(54) METHOD AND APPARATUS FOR ULTRASOUND-GUIDED DELIVERY OF VASCULAR DEVICES

(71) Applicant: Jeko Metodiev Madjarov, Charlotte, NC (US)

(72) Inventor: Jeko Metodiev Madjarov, Charlotte, NC (US)

(73) Assignee: Jeko Metodiev Madjarov, Charlotte, NC (US)

( * ) Notice: Subject to any disclaimer, the term of this patent is extended or adjusted under 35 U.S.C. 154(b) by 0 days.

(21) Appl. No.: 15/310,668

(22) PCT Filed: May 8, 2015

(86) PCT No.: PCT/IB2015/053380
§ 371 (c)(1),
(2) Date: Nov. 11, 2016

(87) PCT Pub. No.: WO2015/173704
PCT Pub. Date: Nov. 19, 2015

(65) Prior Publication Data
US 2017/0119560 A1 May 4, 2017

Related U.S. Application Data

(60) Provisional application No. 61/992,611, filed on May 13, 2014.

(51) Int. Cl.
*A61F 2/95* (2013.01)
*A61F 2/07* (2013.01)
(Continued)

(52) U.S. Cl.
CPC .............. *A61F 2/95* (2013.01); *A61B 1/3137* (2013.01); *A61B 8/0841* (2013.01);
(Continued)

(58) Field of Classification Search
USPC ........... 600/3, 101, 104, 109, 443, 463, 467; 623/1.1–3.1; 606/2, 20, 27, 33, 95.05,
(Continued)

(56) References Cited

U.S. PATENT DOCUMENTS

2005/0090748 A1    4/2005   Makower et al.
2007/0208410 A1*   9/2007   Berra .................. A61F 2/07
                                                    623/1.13
(Continued)

FOREIGN PATENT DOCUMENTS

WO         2014036439 A2      3/2014

OTHER PUBLICATIONS

International Search Report and Written Opinion from corresponding International Application No. PCT/IB2015/053380 dated May 8, 2015.

*Primary Examiner* — Yashita Sharma
(74) *Attorney, Agent, or Firm* — Alston & Bird LLP

(57) ABSTRACT

Delivery devices and vascular devices are described for addressing a target site within a body lumen. The delivery device includes one or more ultrasound transducers positioned to transmit and receive ultrasound signals so as to provide an image of an interior of the patient's blood vessel within which the vascular device is disposed in real time, as the procedure is taking place. Using the images provided by the ultrasound transducers, the longitudinal and rotational position of the delivery device (and the vascular device constrained therein) may be adjusted to align the vascular device with the patient's vasculature. In some examples, the vascular device being delivered includes fenestrations, whereas in others the vascular device integral branch grafts.

8 Claims, 12 Drawing Sheets

(51) Int. Cl.
*A61F 2/06* (2013.01)
*A61F 2/962* (2013.01)
*A61B 1/313* (2006.01)
*A61B 8/08* (2006.01)
*A61B 8/12* (2006.01)
*A61B 90/00* (2016.01)
*A61B 8/00* (2006.01)
*A61F 2/954* (2013.01)

(52) U.S. Cl.
CPC .............. *A61B 8/0891* (2013.01); *A61B 8/12* (2013.01); *A61B 8/4483* (2013.01); *A61B 90/37* (2016.02); *A61F 2/07* (2013.01); *A61F 2/954* (2013.01); *A61F 2/962* (2013.01); *A61B 2090/378* (2016.02); *A61F 2002/061* (2013.01); *A61F 2210/0014* (2013.01); *A61F 2250/0093* (2013.01)

(58) Field of Classification Search
USPC .......................................................... 606/264
See application file for complete search history.

(56) References Cited

U.S. PATENT DOCUMENTS

| 2009/0182405 A1* | 7/2009 | Arnault De La Menardiere ........ A61F 2/856 623/1.11 |
| 2010/0249601 A1 | 9/2010 | Courtney |
| 2010/0280316 A1 | 11/2010 | Dietz et al. |
| 2012/0095340 A1 | 4/2012 | Smith |
| 2012/0123352 A1 | 5/2012 | Fruland et al. |

* cited by examiner

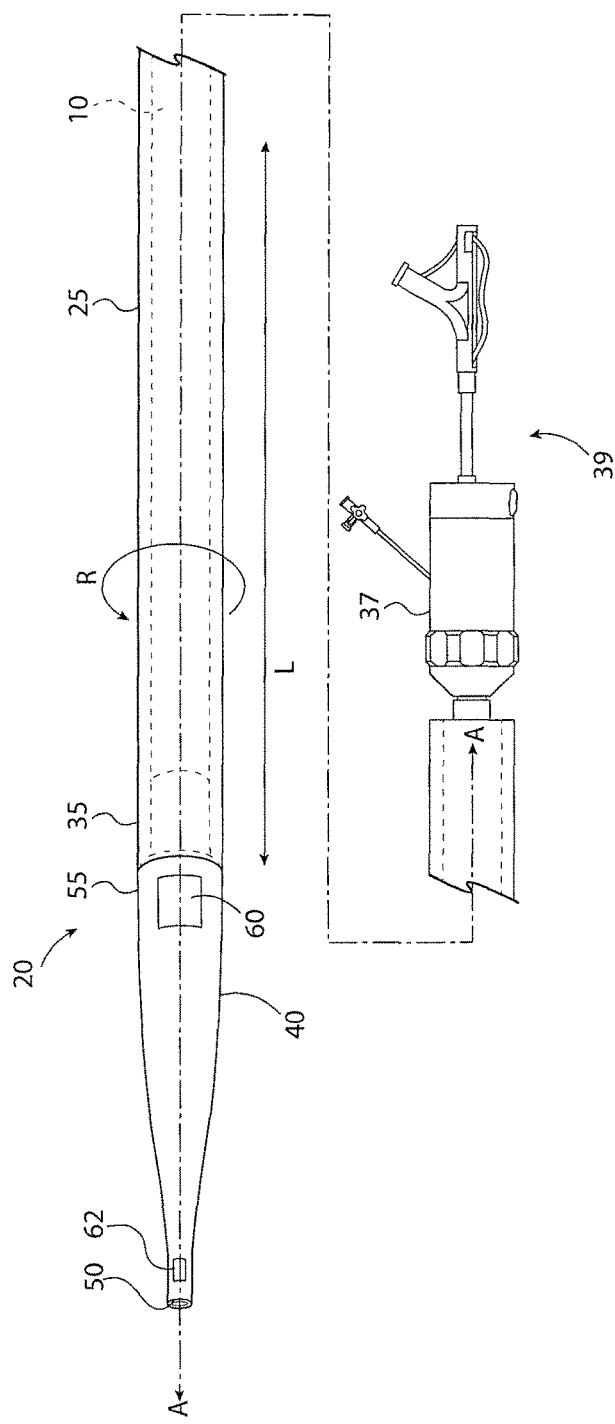
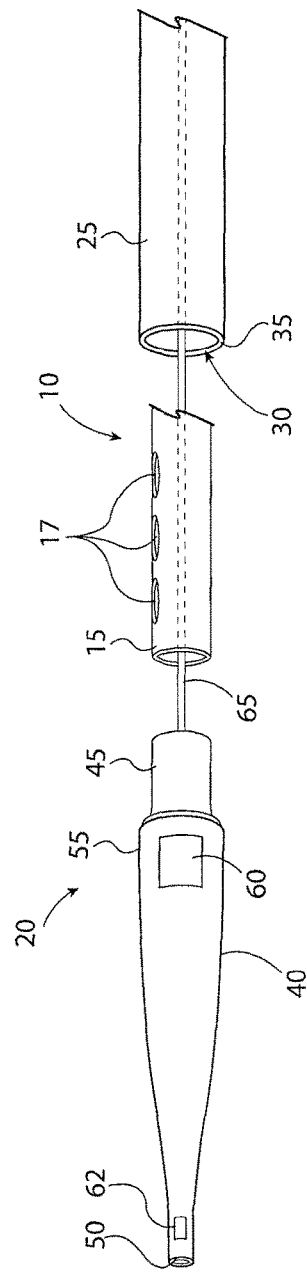
FIG. 2
FIG. 3

METHOD AND APPARATUS FOR ULTRASOUND-GUIDED DELIVERY OF VASCULAR DEVICES

CROSS-REFERENCE TO RELATED APPLICATIONS

This application is a U.S. national stage application under 35 U.S.C. § 371 of International Application No. PCT/IB2015/053380, filed May 8, 2015, which claims priority under 35 U.S.C. § 119 to U.S. Provisional Patent Application No. 61/922,611, filed May 13, 2014, each of which is hereby incorporated by reference in its entirety.

FIELD OF THE INVENTION

The present invention relates generally to methods and apparatuses for endovascular therapy of aortic pathology. More specifically, delivery devices and vascular devices are described for treating vascular abnormalities in the aorta near clusters of arterial branches, such as in the aortic arch proximate the innominate artery, the left carotid artery, and the left subclavian artery, as well as in the visceral segment of the aorta proximate the superior mesenteric artery (SMA), the celiac artery, and the renal arteries.

BACKGROUND

Vascular abnormalities can be serious medical conditions that require prompt and effective treatment. An aneurysm, for example, is a bulging or ballooning portion of the wall of a blood vessel, usually an artery, that is the result of a weakened area of the artery wall. As the aneurysm enlarges, the walls of the artery become thinner, and the risk of rupture increases. A ruptured aneurysm can cause severe hemorrhaging, other complications, and death. Weakened walls of the arteries can be hereditary or can be caused by disease, such as arteriosclerosis.

Conditions such as aneurysms can be treated by reinforcing the artery walls in the weakened areas. For example, vascular devices such as stents, grafts, and stent-grafts can be positioned within the artery proximate the abnormality to preclude blood flow from applying pressure on the damaged area of the vascular wall. Such devices may be delivered to the target site using surgical techniques; however, surgery is invasive and may present additional risks to the health of the patient, especially the elderly.

More recently, intravascular methods have been used to deliver medical devices without requiring surgery. In these cases, a stent-graft, for example, may be delivered to the target site via a delivery catheter that is advanced through the patient's vasculature to the area of the abnormality. The stent-graft, which is carried within the delivery catheter, may be deployed from a distal end of the delivery device and be expanded within the vasculature at the site of the abnormality.

Certain areas of the vasculature can be difficult to treat using traditional intravascular devices and methods. For example, portions of the aorta from which other arteries branch out and/or curved sections of the aorta may pose difficult challenges for the delivery and positioning of a vascular device.

Accordingly, there is a need for a method and apparatus for intravascularly treating aortic abnormalities in a way that improves safety, reproducibility, and ease of administration.

BRIEF SUMMARY

Embodiments of a delivery device are thus described for delivering a vascular device to a target site within a body lumen. The delivery device may comprise an outer sheath defining a first lumen, wherein the outer sheath defines a distal end thereof, and wherein the first lumen is configured to receive a vascular device therein. The delivery device may further comprise a leading member configured to be disposed proximate the distal end of the outer sheath and to be engaged with the outer sheath when the delivery device is in a delivery configuration, and at least one ultrasound transducer disposed proximate an outer surface of the leading member. The ultrasound transducer may be configured to transmit and receive ultrasound signals so as to provide an image of an interior of the patient's blood vessel within which the vascular device is disposed proximate the location of the distal end of the outer sheath, such that a longitudinal position and a rotational position of the vascular device with respect to the patient's blood vessel and surrounding anatomical structures may be determined and may be adjusted through manipulation of the delivery device based on the image provided.

In some cases, the delivery device may comprise an inner sheath at least partially disposed within the first lumen of the outer sheath and configured to be axially movable with respect to the outer sheath. The inner sheath may define a second lumen and a distal end thereof, and the second lumen may be configured to receive the vascular device therein. The vascular device may comprise a main body and at least one branch graft extending from the main body and configured to be aligned with and extended into an arterial branch. The inner sheath may comprise a slot configured to extend around the at least one branch graft. The slot may comprise an open end and a closed end, wherein the closed end is disposed proximally of the open end, and wherein the open end corresponds to the distal end of the inner sheath, such that the inner sheath is configured to deploy the main body of the vascular device without constraining the at least one branch graft.

In some embodiments, the vascular device may be self-expandable.

The at least one ultrasound transducer may be a first ultrasound transducer, and the delivery device may further comprise a second ultrasound transducer disposed proximate the outer surface of the leading member. The first ultrasound transducer may be configured to transmit and receive ultrasound signals so as to provide an image of an interior of a first portion of the patient's blood vessel within which the vascular device is disposed adjacent the vascular device. The second ultrasound transducer may be configured to transmit and receive ultrasound signals so as to provide an image of an interior of a second portion of the patient's blood vessel within which the vascular device is disposed distally of the leading member. In some cases, the at least one ultrasound transducer may be wireless.

In other embodiments, an assembly for delivering a vascular device to a target site within a body lumen is provided, where the assembly comprises a vascular device configured to treat a target site within a body lumen and a delivery device configured to deliver the vascular device to the target site. The delivery device may comprise an outer sheath defining a first lumen, wherein the outer sheath defines a distal end thereof, and wherein the first lumen is configured to receive the vascular device therein; a leading member configured to be disposed proximate the distal end of the outer sheath and to be engaged with the outer sheath when the delivery device is in a delivery configuration; and at least one ultrasound transducer disposed proximate an outer surface of the leading member. The ultrasound transducer may be configured to transmit and receive ultrasound signals so as to provide an image of an interior of the patient's blood vessel within which the vascular device is disposed proximate the location of the distal end of the outer sheath, such that a longitudinal position and a rotational position of the vascular device with respect to the patient's blood vessel and surrounding anatomical structures may be determined and may be adjusted through manipulation of the delivery device based on the image provided.

In some cases, the delivery device may further comprise an inner sheath at least partially disposed within the first lumen of the outer sheath and configured to be axially movable with respect to the outer sheath, wherein the inner sheath defines a second lumen and a distal end thereof, and wherein the second lumen is configured to receive the vascular device therein. The vascular device may comprise a main body and at least one branch graft extending from the main body and configured to be aligned with and extended into an arterial branch, wherein the inner sheath comprises a slot configured to extend around the at least one branch graft. The vascular device may comprise two branch grafts. In some embodiments, the slot may comprise an open end and a closed end, wherein the closed end is disposed proximally of the open end, and wherein the open end corresponds to the distal end of the inner sheath, such that the inner sheath is configured to deploy the main body of the vascular device without constraining the branch graft. Moreover, the at least one branch graft may be configured to be disposed between the inner sheath and the outer sheath when the assembly is in the delivery configuration. The vascular device may be self-expandable.

In some cases, the vascular device may be a first vascular device, wherein the first vascular device is configured to receive a second vascular device through an end of the first vascular device and to engage the second vascular device via an integral landing zone formed proximate the end receiving the second vascular device.

In some embodiments, the at least one ultrasound transducer may be a first ultrasound transducer, and the delivery device may further comprise a second ultrasound transducer disposed proximate the outer surface of the leading member. The first ultrasound transducer may be configured to transmit and receive ultrasound signals so as to provide an image of an interior of a first portion of the patient's blood vessel within which the vascular device is disposed distally of the leading member. The second ultrasound transducer may be configured to transmit and receive ultrasound signals so as to provide an image of an interior of a second portion of the patient's blood vessel within which the vascular device is disposed adjacent the vascular device.

In still other embodiments, a method for positioning a vascular device proximate a target site within a body lumen may be provided. The method may comprise advancing toward a target site within the body lumen an assembly comprising a delivery device with a vascular device disposed therein. The delivery device may be in a delivery configuration and may comprise an outer sheath defining a first lumen, wherein the outer sheath defines a distal end thereof, and wherein the first lumen is configured to receive the vascular device therein. The delivery device may further comprise a leading member configured to be disposed proximate the distal end of the outer sheath and to be engaged with the outer sheath when the delivery device is in a delivery configuration.

The method may further comprise viewing an image of an interior of the patient's blood vessel within which the vascular device is disposed proximate the location of the distal end of the outer sheath, wherein the image is provided via at least one ultrasound transducer disposed proximate an outer surface of the leading member; adjusting at least one of a longitudinal position or a rotational position of the delivery device with reference to the image; and moving the outer sheath proximally with respect to the vascular device to deploy the vascular device at the target site.

In some cases, the vascular device may comprise a main body and at least one branch graft extending from the main body and configured to be aligned with and extended into an arterial branch. Moving the outer sheath may comprise moving the outer sheath to deploy the at least one branch graft, and the method may further comprise aligning the at least one branch graft with an opening of an arterial branch, such that the at least one branch graft extends into the arterial branch with reference to the image, and moving an inner sheath with respect to the outer sheath, wherein the inner sheath is at least partially disposed within the first lumen of the outer sheath and surrounds the main body of the vascular device, and wherein movement of the inner sheath serves to deploy the main body of the vascular device. The method may further comprise moving the leading member proximally through the deployed vascular device to remove the delivery device from the body lumen.

The at least one ultrasound transducer may, in some cases, be a first ultrasound transducer, and the delivery device may further comprise a second ultrasound transducer disposed proximate the outer surface of the leading member. The method may further comprise viewing a first image provided via the first ultrasound transducer, wherein the first image shows an interior of a first portion of the patient's blood vessel within which the vascular device is disposed adjacent the vascular device, and viewing a second image provided via the second ultrasound transducer, wherein the second image shows an image of an interior of a second portion of the patient's blood vessel within which the vascular device is disposed distally of the leading member.

BRIEF DESCRIPTION OF THE DRAWINGS

Figure 1:
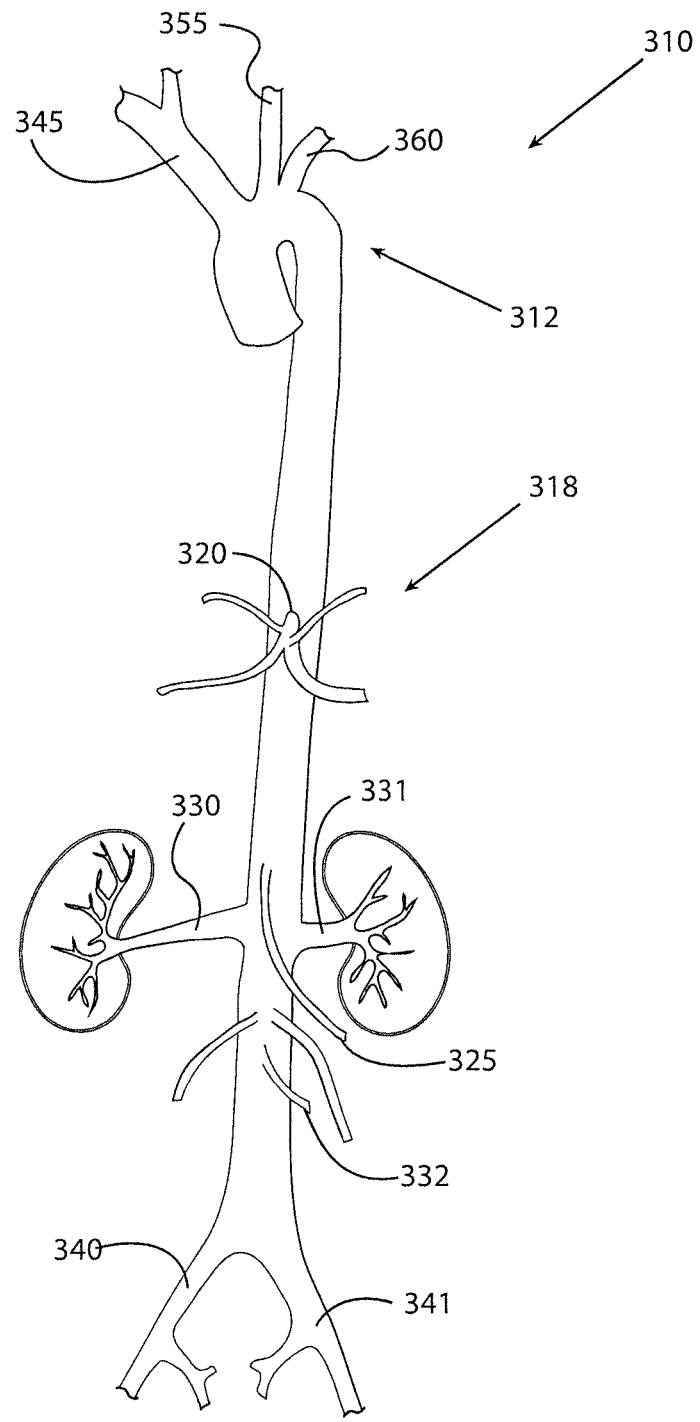
Figure 4:
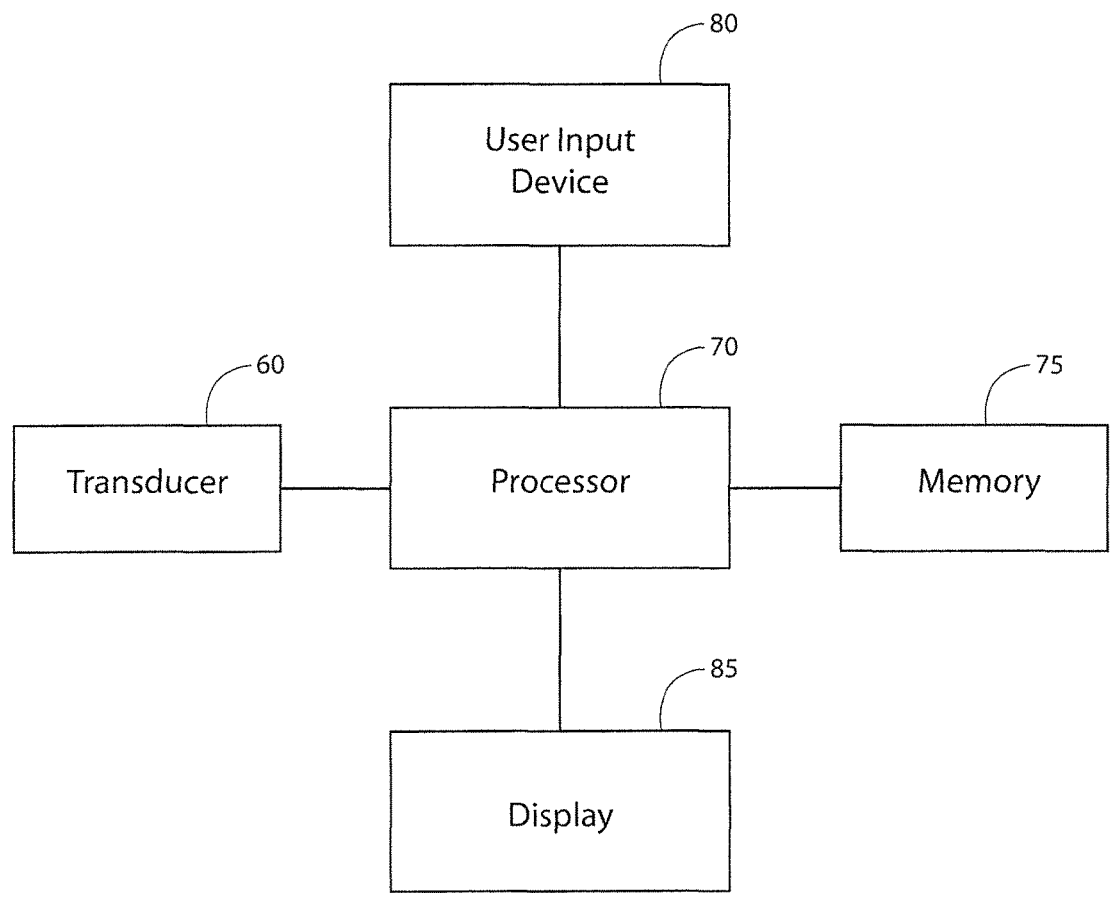
Figure 5:
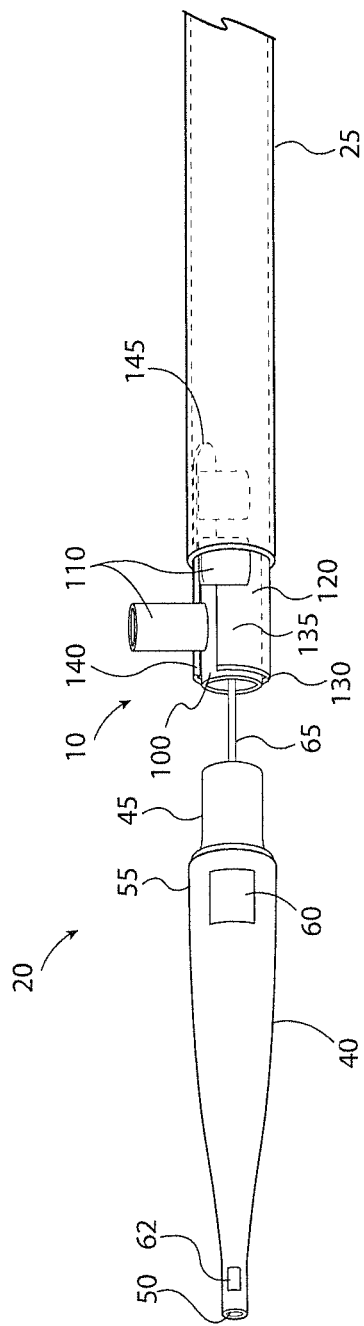
Figure 6:
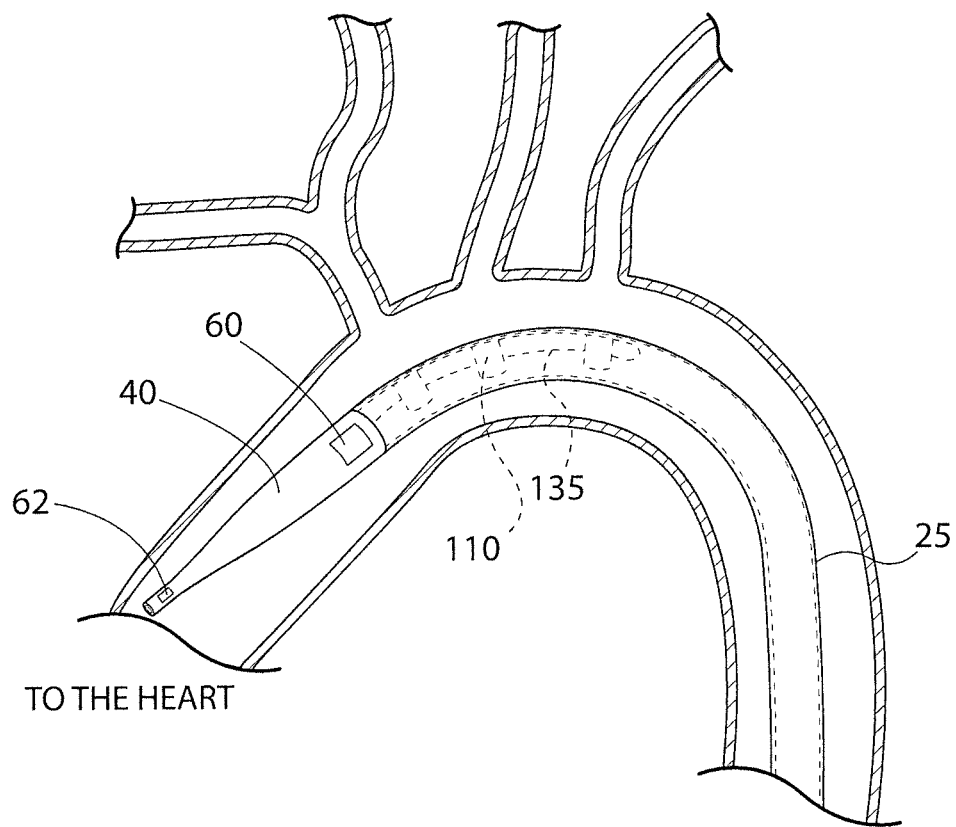
Figure 7:
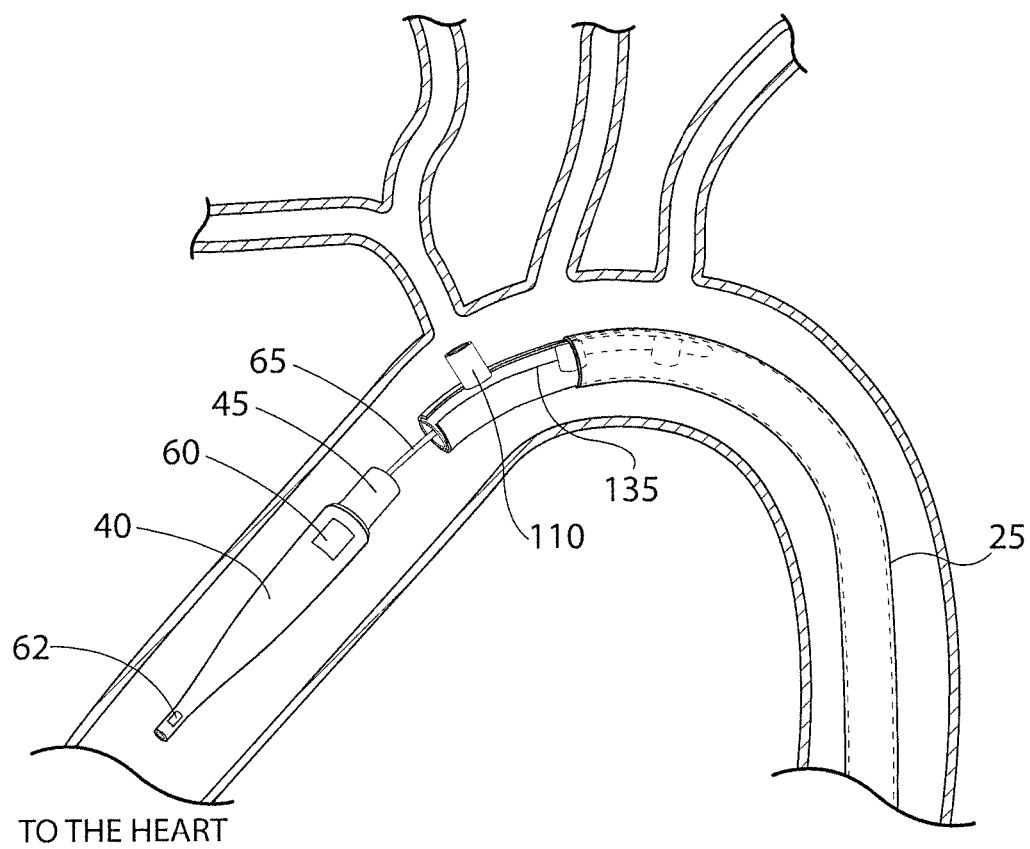
Figure 8:
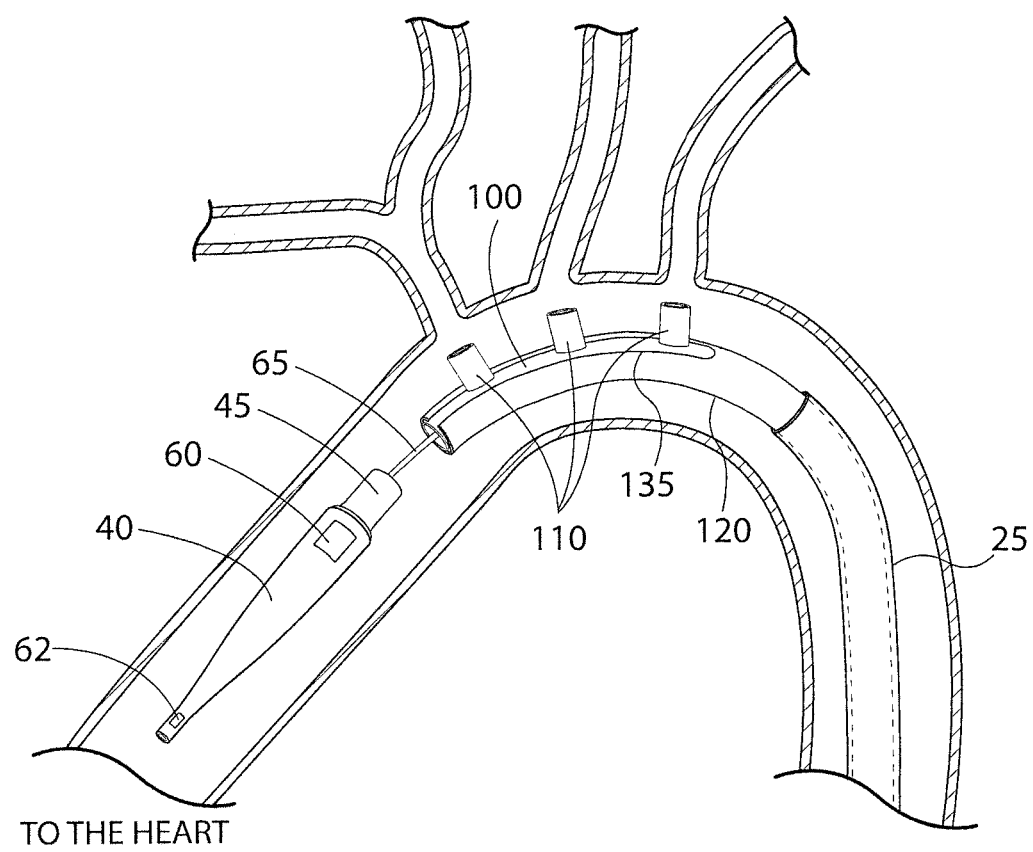
Figure 9:
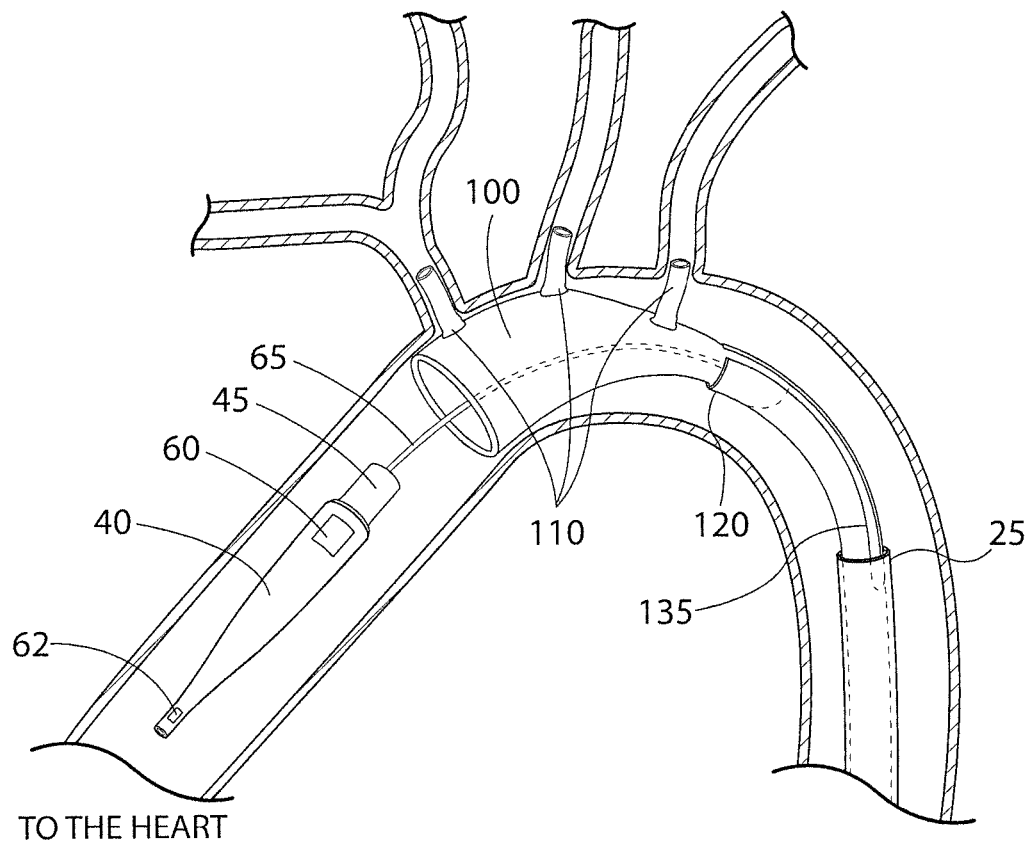
Figure 10:
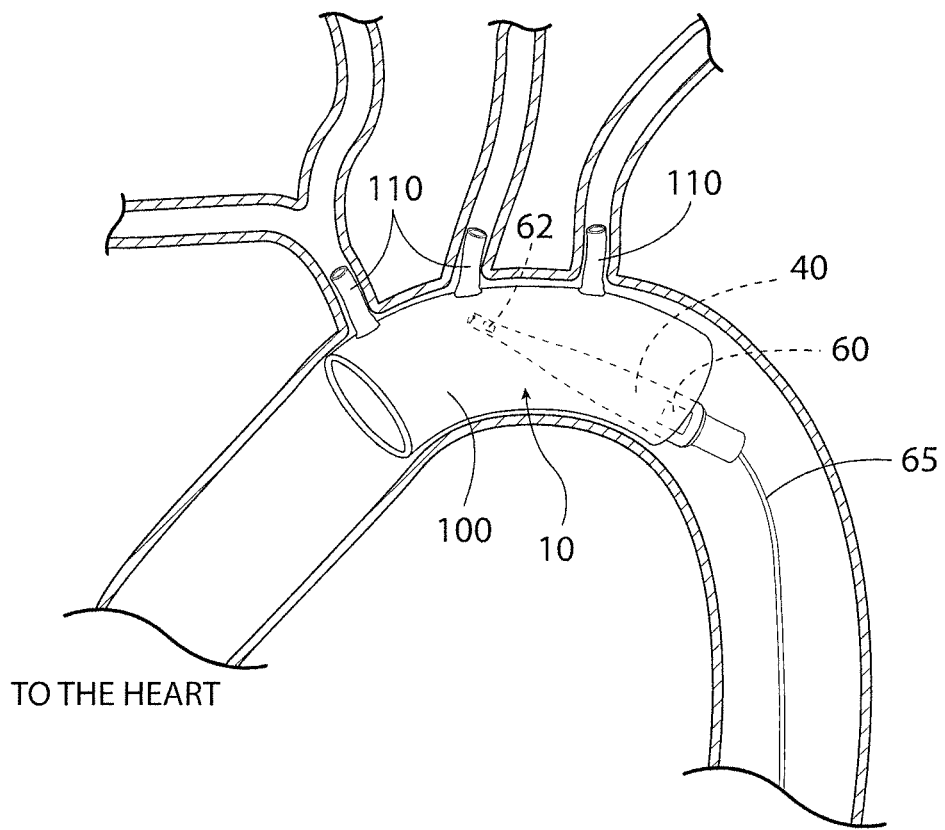
Figure 11:
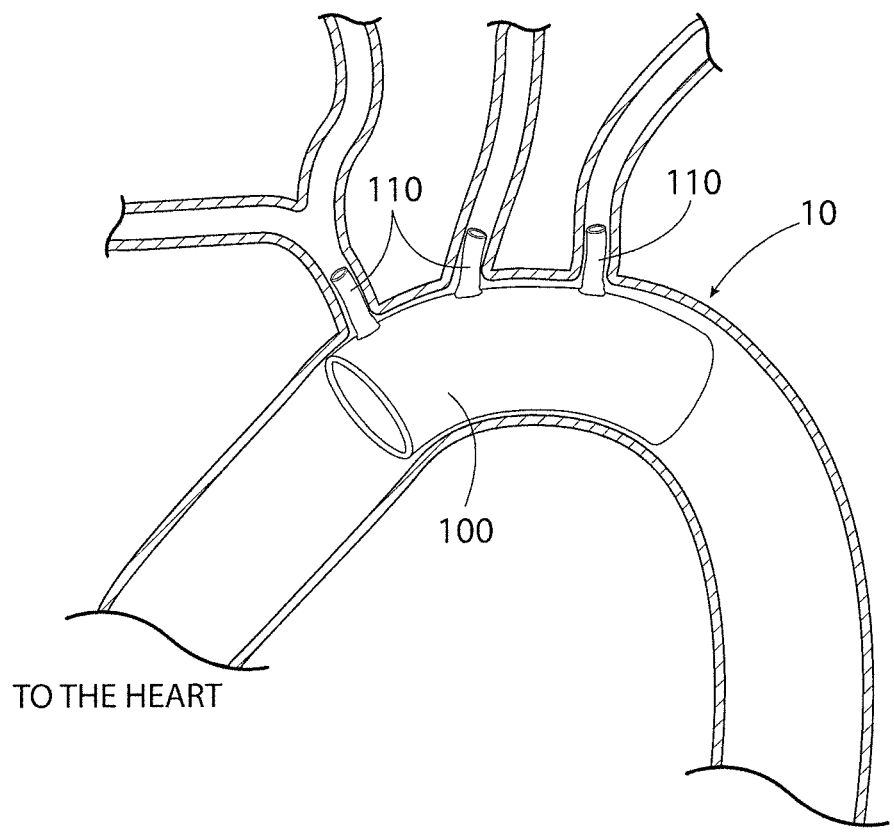
Figure 12A:
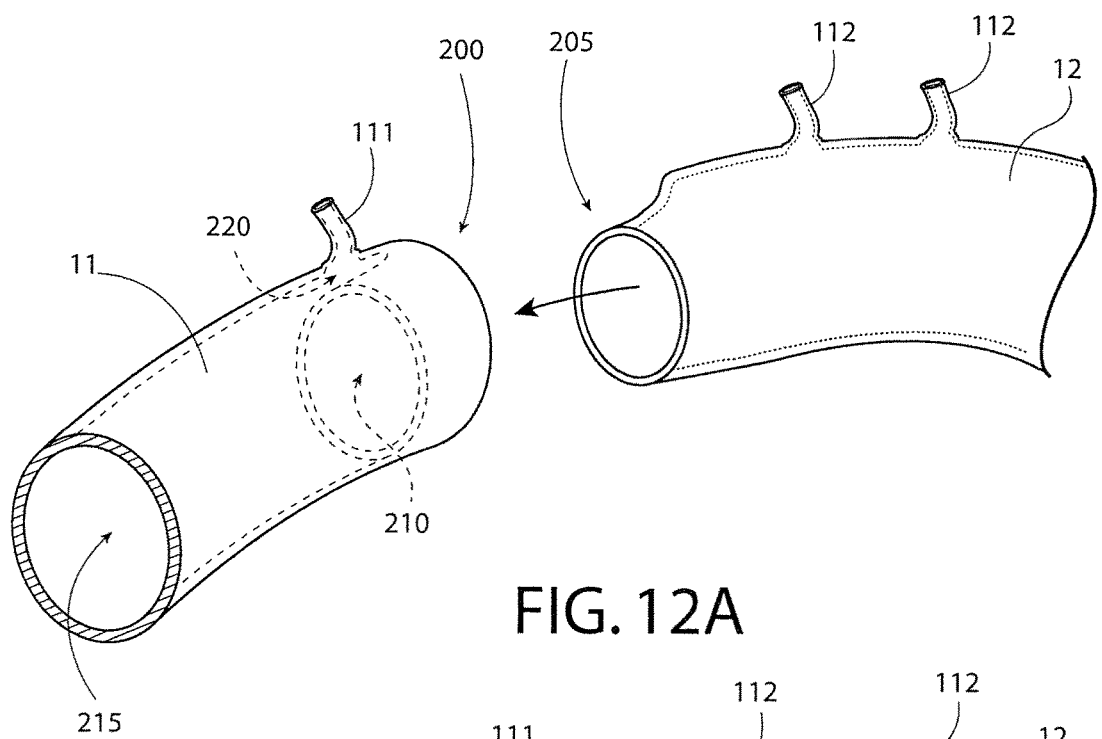
Figure 12B:
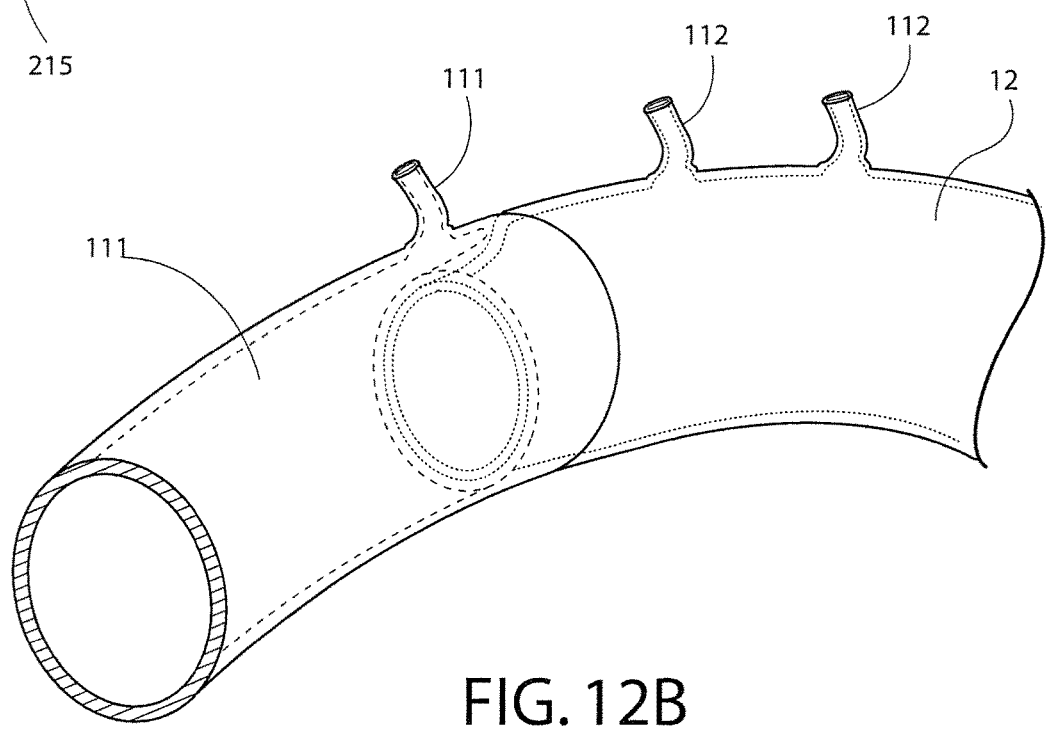
Figure 13:
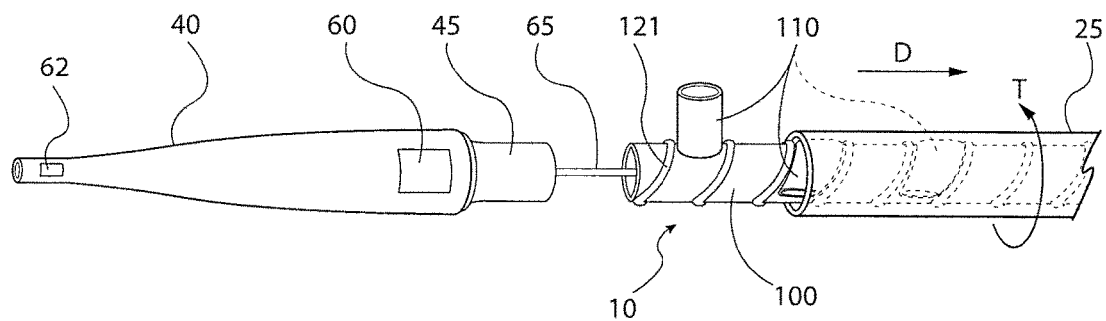
Figure 14:
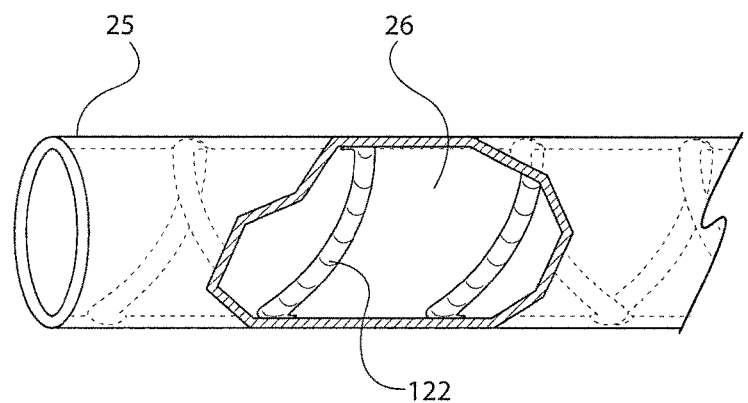

Having thus described the invention in general terms, reference will now be made to the accompanying drawings, which are not necessarily drawn to scale, and wherein:

FIG. 1 shows a schematic representation of an aorta with arterial branches;

FIG. 2 shows a schematic representation of a delivery device with a vascular device held therein in accordance with an exemplary embodiment of the present invention;

FIG. 3 shows a perspective, partially-exploded view of a delivery device holding a vascular device including fenestrations in accordance with an exemplary embodiment of the present invention;

FIG. 4 shows a system for receiving ultrasound images via an ultrasound transducer that is provided on a vascular device in accordance with an exemplary embodiment of the present invention;

FIG. 5 shows a schematic view of a delivery device holding a partially deployed vascular device including branch grafts, where the delivery device includes an inner sheath and an outer sheath in accordance with an exemplary embodiment of the present invention;

FIG. 6 shows a schematic view of a delivery device holding a vascular device including branch grafts, where the delivery device is positioned proximate the target site in a delivery configuration in accordance with an exemplary embodiment of the present invention;

FIG. 7 shows a schematic view of the delivery device of FIG. 6, where one of the branch grafts is deployed via movement of an outer sheath of the delivery device in accordance with an exemplary embodiment of the present invention;

FIG. 8 shows a schematic view of the delivery device of FIG. 6, where three branch grafts are deployed via movement of an outer sheath of the delivery device in accordance with an exemplary embodiment of the present invention;

FIG. 9 shows a schematic view of the delivery device of FIG. 6, where a main body of the vascular device is partially deployed via movement of an inner sheath of the delivery device in accordance with an exemplary embodiment of the present invention;

FIG. 10 shows a schematic view of the vascular device and the delivery device of FIG. 6, where the vascular device is deployed and engages the arterial branches and the leading member of the delivery device is being withdrawn from the vascular device in accordance with an exemplary embodiment of the present invention;

FIG. 11 shows a schematic view of the vascular device of FIG. 6, where the vascular device is fully deployed and is in engagement with the native vessel in accordance with an exemplary embodiment of the present invention;

FIG. 12A shows a schematic representation of a first vascular device and a second vascular device for addressing a pathology in the aortic arch prior to engagement of the respective ends in accordance with an exemplary embodiment of the present invention;

FIG. 12B shows a schematic representation of the first vascular device and the second vascular device of FIG. 12A following engagement of the respective ends in accordance with an exemplary embodiment of the present invention;

FIG. 13 shows a schematic view of a delivery device with a partially deployed vascular device including branch grafts therein, where the delivery device includes an inner sheath in the form of a coil in accordance with an exemplary embodiment of the present invention; and FIG. 14 shows the outer sheath of FIG. 13 including grooves in an interior surface of the outer sheath in accordance with an exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" refer to a location farthest from a reference point, such as the point of entry into the body lumen or the operator of a delivery device; the terms "proximal" and "proximally" refer to a location closest to the reference point. Furthermore, although the examples described herein refer to aneurysms in the ascending aorta and the aortic arch and/or the abdominal aorta, embodiments of the described invention may be used to treat various vascular abnormalities, including aneurysms, type A dissections, and type B acute dissections, in various locations, including the ascending aorta, the aortic arch, the thoracic aorta, and other blood vessels.

Referring now to FIG. 1, a schematic representation of an aorta 310 is shown. Thoracoabdominal aortic pathologies are often considered some of the most difficult aortic pathologies to treat. The ascending aorta and the aortic arch 312, for example, are sections that include a high degree of curvature, as well as arteries that branch up to feed oxygenated blood to the head, neck, and arms. Such arteries include the innominate artery 345, the left common carotid artery 355, and the left subclavian artery 316.

The abdominal aorta 318, which begins at the diaphragm, also includes several important arterial branches that feed most of the major organs. Such arteries include the celiac artery 320, the superior mesenteric artery (SMA) 325, the renal arteries 330, 331, the inferior mesenteric artery (IMA) 332, and the femoral arteries 340, 341. Aortic abnormalities, such as aneurysms and dissections (e.g., a tear in the inner wall of the aorta that creates a false lumen between the layers of the wall of the aorta), can be extremely difficult to treat when they occur in sections of the aorta that include a number of arterial branches, such as in the aortic arch and the abdominal aorta, for example.

In particular, the delivery of conventional vascular devices to target sites such as the aortic arch and/or the abdominal aorta can, at times, cause further injury to the patient or otherwise complicate a pre-existing medical condition. A misdirected delivery device, for example, may inadvertently puncture the arterial wall, enter a false lumen and exacerbate a dissection, or deploy the vascular device at the wrong location or in the wrong orientation. Deployment of a vascular device can be further complicated in the location of clusters of arterial branches, such as in the aortic arch proximate the innominate artery 345, the left common carotid artery 355, and the left subclavian artery 360, and in the visceral aorta proximate the celiac artery, SMA, and renal arteries. In such locations, the vascular device, which may be designed to also address the arterial branches in one way or another, may need to be accurately positioned such that features of the vascular device (e.g., fenestrations, or openings in the walls of the device) are aligned with the openings to the arterial branches and do not unintentionally block or limit blood flow to these branches.

In conventional delivery systems, the operator (e.g., the surgeon) is often deploying the vascular device "on the blind." Although imaging techniques including fluoroscopy and/or angiography may be used to help the operator to identify the approximate location of the delivery device and/or vascular device as it is advanced from a point of entry into the body lumen to the target site, such techniques are not conducive to a real-time assessment of the three-dimensional position of the delivery device and vascular device. For example, such techniques may be used prior to delivery of the vascular device, such as to facilitate the positioning of a guidewire proximate the target site, and/or after deployment of the vascular device to confirm that the device has been placed in the correct location; however, such techniques do not typically allow the operator to check the positioning of the delivery device and vascular device and/or the deployment of the vascular device as the procedure is taking place. For example, even when the vascular device appears to be accurately positioned as originally placed, the natural expansion and contraction of the aorta with each heartbeat may cause the position to shift prior to full deployment.

Moreover, conventional imaging techniques that are typically used to guide delivery and deployment of vascular devices generally provide the operator with a two-dimensional image. For procedures in which the rotational position of the vascular device is important, such as when the vascular device is to be aligned with arterial branches, the operator may not have enough visual data to confirm whether the three-dimensional orientation is accurate.

Accordingly, embodiments of the present invention may help provide for a vascular device and delivery system for addressing aortic pathologies. The vascular device may have different configurations to address different types of pathologies. In some embodiments, for example, the vascular device may be a simple, tubular device (e.g., a stent graft) having no fenestrations or branch grafts, such as may be suitable for deployment at a target site where the blood vessel has no arterial branches. The vascular device may be self-expandable and may be configured similarly to conventional vascular devices. In other cases, as described in greater detail below and depicted in FIGS. 5-10, the vascular device 10 may comprise a main body and at least one branch graft, such as may be suitable for extending into an arterial branch at the target site. In still other cases, as described in greater detail below and depicted in FIGS. 12A and 12B, the vascular device may comprise two components 11, 12 that are configured to engage each other and act as one device.

Regardless of the configuration of the vascular device, embodiments of the present invention provide a delivery device 20 that is configured to deliver and deploy the vascular device at the target site while allowing the operator to view real-time images of the patient's vasculature proximate the delivery device as the delivery device is advanced to the target site and as the vascular device is being deployed. Thus, with reference to FIGS. 2 and 3 and as described in greater detail below, embodiments of the delivery device 20 may comprise at least an outer sheath 25 defining a first lumen 30 and a distal end 35 and may further include a leading member 40. The first lumen 30 may be configured to receive a vascular device 10 therein. For example, in embodiments in which the vascular device 10 is self-expandable, the outer sheath may be configured to radially constrain the vascular device while the vascular device is within the delivery device 20.

The leading member 40 may be configured to be disposed proximate the distal end 35 of the outer sheath 25 and to be engaged with the outer sheath when the delivery device is in a delivery configuration, such as the configuration shown in FIG. 2, in which the vascular device 10 is wholly received within the delivery device 20 (e.g., wholly constrained by the outer sheath 25). In this regard, a proximal end 45 of the leading member 40 may be configured to attach to the distal end 35 of the outer sheath 25, such as via an interference fit, a threaded connection, etc.

In some embodiments, the leading member 40 may be configured to have a generally tapered shape, such that a distal tip 50 of the leading member has a smaller diameter than the exposed proximal portion 55 of the leading member (e.g., the portion of the proximal end 45 that abuts the distal end 35 of the outer sheath 25 in the delivery configuration and forms an exterior surface of the delivery device along with the outer sheath). The diameter of the leading member 40 may, in some embodiments, gradually increase along a longitudinal axis A of the delivery device 20 (shown in FIG. 2) from the distal tip 50 to the exposed proximal portion 55, thereby facilitating the advancement of the delivery device from the entry point into the body lumen, through the patient's blood vessel, to the target site.

According to some embodiments, at least one ultrasound transducer 60 may be disposed proximate an outer surface of the leading member 40. The ultrasound transducer may be configured to transmit and receive ultrasound signals so as to provide an image of an interior of the patient's blood vessel within which the vascular device is disposed proximate the location of the distal end 35 of the outer sheath. In this way, a longitudinal position and a rotational position of the vascular device with respect to the patient's blood vessel and surrounding anatomical structures may be determined. The longitudinal position may be, e.g., the linear position of the vascular device 10 along the length of the blood vessel, depicted by the arrow L in FIG. 2. The rotational position may be, e.g., the angular position of the vascular device 10 about its longitudinal axis A and with respect to the vessel wall circumference, depicted by the arrow R in FIG. 2. The longitudinal position and the rotational position may be adjusted (e.g., in the directions L and R, respectively) through manipulation of one or more handle components (shown generally as reference 37) at a proximal end 39 of the delivery device 20 based on the image provided via the ultrasound transducer 60, as described in greater detail below.

The ultrasound transducer 60 may, in some embodiments, be configured for 2D and/or 3D trans-esophageal echocardiography (TEE) or intracardiac echocardiography (ICE). In one embodiment, the ultrasound transducer 60 may comprise an active transducer material that is able to generate ultrasonic sound waves in response to an applied electric field. In particular, the transducer may comprise a material that generates an inverse piezoelectric effect in response to an applied electric field. Piezoelectric effect is manifested by the appearance of an electric potential across the faces of some materials when they are placed under pressure. When, on the other hand, a piezoelectric material (PEM) is subjected to an electric field, physical stresses are created in the material that distorts it, a phenomenon known as the inverse piezoelectric effect.

A wide variety of PEMs are currently known. Among these are crystalline substances whose unit crystal structure lacks a center of symmetry. Examples, without limitation of such substances are tourmaline, Rochelle salt and quartz. Polycrystalline substances which have been placed in a polarized state can also exhibit a piezoelectric effect and are called piezoelectric ceramics. Examples of piezoelectric ceramics include, without limitation, barium titanate (BaTiO$_3$) and lead zirconium titanate (PZT, PbZrTiO$_3$). In addition to piezoelectric crystals and ceramics, a number of polymeric materials are known to exhibit a piezoelectric effect. Most notable among these is polyvinylidene fluoride (PVDF) which was discovered by Kawai in 1969 and is still today the polymer that exhibits the strongest piezoelectric effect. Some co-polymers of PVDF, such as poly(PVDF-co-trifluoroethylene) and poly(PVDF-co-tetrafluoroethylene) are also piezoelectric. Other polymers that exhibit a piezoelectric effect include, without limitation, polyparaxylene, poly(bischloromethyloxetane) (Penton), aromatic polyamides, polysulfone, polyvinyl fluoride, synthetic polypeptides and cyanoethylcellulose.

The electrical signal sent to the piezoelectric member may constitute any number of waveforms. For example, without limitation, the signal may consist of a single DC pulse, multiple DC pulses, a continuous sinusoidal signal, or an oscillating square wave signal. Any type of signal may be employed that will initiate the converse piezoelectric effect in the piezoelectric member. Many signal types other than those exemplified herein will become apparent to those skilled in the art based on the disclosures herein and all such signal types are within the scope of this invention.

In other aspects, the ultrasound transducer 60 may comprise a passive transducer. In one such aspect, the transducer comprises a passive transducer that is an echogenic material that is configured to enhance visualization of the transducer, and hence the position and alignment of the delivery device and/or vascular device, via echocardiography. In one embodiment, the passive transducer comprises a material that is configured to be detectable via the reflection of a signal to which the passive transducer has been exposed.

In some embodiments as described above, one or more piezoelectric crystals of the ultrasound transducer 60 may be integrated into the leading member 40 of the delivery device 20, and lead wires from the ultrasound transducer may be routed along a core member 65 (e.g., shown in FIG. 3) to an environment external to the patient's body. The core member 65 may, for example, comprise one or more wires, which may be overwrapped to form a unitary structure. Moreover, in some embodiments, the core member 65 may define a lumen that is configured to receive a guidewire therethrough, such that the delivery device 20 and vascular device 10 may be delivered over a guidewire, e.g., using the Seldinger technique. In some embodiments, however, the ultrasound transducer 60 may be wireless, such that it may be configured to communicate with a processor (described below) without the routing of any leads.

Accordingly, the ultrasound transducer 60 may be configured to transmit ultrasound signals in the vicinity of the ultrasound transducer and to receive ultrasound signals (e.g., return signals) based on the transmitted signals that are indicative of the structure and anatomy of the blood vessel and surroundings of the delivery device 20 at any given time. The transmission of ultrasound signals may be generally continuous, with the frequency, amplitude, etc., of the signals being configurable by the operator.

With reference to FIG. 4, the transducer 60 may be configured to communicate (e.g., via one or more wires of the core member 65) with a processor 70, which may be located externally of the patient's body. Electrical signals from the ultrasound transducer 60 corresponding to the ultrasound signals received as return signals may be transmitted to the processor 70 for processing. The processor 70 may be embodied in a number of different ways. For example, the processor 70 may be a coprocessor, a microprocessor, a controller, or various other processing circuitry including integrated circuits.

The processor 70 may be in communication with at least one memory 75, and the processor may be configured to execute instructions stored in the memory or that are otherwise accessible to the processor. In embodiments in which the processor 70 is embodied as an executor of software instructions, the instructions may specifically configure the processor to perform the algorithms and/or operations for analyzing the ultrasound signals received as return signals by the ultrasound transducer 60 and generating an image corresponding to the blood vessel interior being imaged. The memory 75, which may include volatile memory, such as volatile Random Access Memory (RAM), and/or non-volatile memory, may store any of a number of pieces of information and data, including software programs, applications, files, etc. that are used to implement the functions described herein.

With continued reference to FIG. 4, the processor 70 may further be in communication with a user input device 80 and a display 85. The user input device 80 may be one or more of a keyboard, mouse, touchpad, touchscreen, etc., that is configured to receive input from a user (e.g., the operator of the delivery device) and convey the input to the processor 70. The user input device 80 may, for example, be configured to receive input from the operator of the delivery device regarding the ultrasound signals being transmitted by the ultrasound transducer 60, such as to initiate or terminate the transmission of the ultrasound signals, increase or decrease the frequency, etc. The user input device 80 may further be configured to adjust certain features of the image being provided via the display 85, such as the brightness, sharpness, contrast level, etc. to achieve a clearer image. In this regard, the display 85 may be any computer output surface and/or projecting mechanism that is configured to show text and/or graphic images to the user, such as via cathode ray tube (CRT), liquid crystal display (LCD), light-emitting diode, gas plasma, or other image projection technology. In some embodiments, the processor 70, memory 75, user input device 80, and/or display 85 may be embodied by a single apparatus, such as a computer.

Accordingly, embodiments of the present invention are configured to provide the operator with an image of the interior of the patient's blood vessel in the vicinity of the ultrasound transducer 60 as the delivery device 20 is being advanced to the target site, such that the operator may be able to manipulate the delivery device 20 to adjust its position and orientation to guide it to the appropriate target site in a manner that is more efficient, accurate, and safe. Moreover, once the delivery device 20 is at the target site, images generated based on the ultrasound signals transmitted and received by the ultrasound transducer 60 may be used to assess the accuracy of the deployment of the vascular device 10 from the delivery device 20, as well as to facilitate withdrawal and removal of the delivery device once the vascular device has been deployed and is engaged with the body lumen, as described in greater detail below.

Turning again to FIG. 3, the core member 65 may be configured to extend from the leading member 40 to a handle 37 (shown in FIG. 2). The handle 37 may be configured to be manipulated by the operator to move the leading member, the outer sheath 25, and the vascular device 10 held therein, as a unit, to advance the delivery device through the body lumen to the target site and to adjust the longitudinal position of the delivery device (e.g., by moving the delivery device proximally and distally with respect to the blood vessel) when the delivery device is in the delivery configuration shown in FIG. 2. Once the assembly 10, 20 is positioned generally in the location of the target site, the outer sheath 25 may be disengaged from the leading member 40 (e.g., through an uncoupling of the distal end 35 of the outer sheath from the proximal end 45 of the leading member) to allow the outer sheath to be moved proximally with respect to the vascular device 10 and the leading member. In this regard, the core member 65 may be held stationary by the operator at a proximal end of the delivery device (not shown) to hold the leading member 40 stationary while the outer sheath 25 is moved proximally with respect to the leading member 40 and the vascular device 10.

As the outer sheath 25 is moved with respect to the vascular device 10 and portions of the vascular device 10 are no longer constrained by the outer sheath, in some embodiments the vascular device may be configured to self-expand to engage the walls of the blood vessel at the location of the target site. Because the outer sheath 25 may remain engaged to at least a portion of the vascular device 10 as the vascular device is in the process of being deployed, the position of the assembly (e.g., the vascular device 10 and the delivery device 20) may continue to be adjusted, longitudinally and rotationally, by the operator via manipulation of a proximal end of the delivery device (not shown), as needed, to properly orient and align the vascular device with the target site. For example, by monitoring the images provided via the ultrasound transducer 60 during the unsheathing of the vascular device 10, the real-time position of the vascular device prior to full deployment may be evaluated and adjusted on a continuous basis to achieve a more accurate positioning, as described in greater detail below.

When the outer sheath 25 has been fully withdrawn to allow the vascular device 10 to expand over its entire expandable length, the core member 65 may be moved proximally with respect to the deployed vascular device to move the leading member 40 back through the deployed vascular device towards the operator. In this way, the leading member 40 may be removed from the body lumen, leaving the vascular device 10 in place at the target site.

As shown in FIGS. 2 and 3, as an example, in some embodiments the delivery device 20 may include more than one ultrasound transducer disposed in different locations on the leading member 40. For example, the at least one ultrasound transducer 60 may be a first ultrasound transducer, and the delivery device 20 may further include a second ultrasound transducer 62 disposed proximate the outer surface of the leading member 40. The first ultrasound transducer 60, as described above, may be configured to transmit and receive ultrasound signals so as to provide an image of an interior of a first portion of the patient's blood vessel within which the vascular device 10 is disposed adjacent the vascular device, such as proximate the location of the distal end 35 of the outer sheath 25 when the vascular device and the delivery device are in the delivery configuration shown in FIG. 2.

As the outer sheath 25 is moved proximally with respect to the vascular device 10, the first ultrasound transducer 60 may be configured to transmit and receive ultrasound signals so as to provide an image of the interior of the patient's blood vessel proximate a distal end 15 of the vascular device 10. In this way, in some embodiments as depicted in FIG. 3, for example, the first ultrasound transducer 60 may be configured to provide a zone of coverage for the ultrasound image that provides a view of one or more fenestrations 17 that are configured to align with arterial branches, such that proper positioning and alignment of the fenestrations with the arterial branches may be facilitated during deployment of the vascular device 10. The first ultrasound transducer 60 may, for example, be configured to provide a zone of coverage that extends over a viewing area of approximately 45° to approximately 180° or more.

The second ultrasound transducer 62 may be configured to transmit and receive ultrasound signals so as to provide an image of an interior of a second portion of the patient's blood vessel within which the vascular device is disposed distally of the leading member 40. For example, with reference to the delivery configuration shown in FIG. 2, the second ultrasound transducer 62 may be configured to provide an image of a region of the blood vessel "in front of" the delivery device 20, distally and in the vicinity of the distal tip 50, as the delivery device is advanced through the patient's vasculature. The second ultrasound transducer 62 may, for example, be configured to provide a zone of coverage that extends over a viewing area of approximately 45° to approximately 360°. Moreover, in some embodiments, the first and second ultrasound transducers 60, 62 may be selected and positioned to provide zones of coverage that, to some extent, overlap with each other.

Images from the first and second ultrasound transducers 60, 62 may be provided to the operator (e.g., via the display 85 of FIG. 4) simultaneously in some cases, such as on different displays arranged for viewing by the operator or in different windows or areas provided on the same display. In this way, the operator may be able to monitor the longitudinal position of the delivery device 20 (e.g., as the delivery device is being advanced through the patient's vasculature), as well as the rotational position of the delivery device with respect to the anatomical surroundings of the delivery device (e.g., the real-time orientation of the delivery device) during advancement, and also during deployment. Images provided via one or both transducers 60, 62 may further be used by the operator to determine whether the vascular device 10 is being properly deployed (e.g., deployed at the correct longitudinal and rotational positions with respect to the target site). Once the vascular device 10 is deployed and is engaged with the blood vessel and any surrounding anatomical structures as necessary, the images from one or both transducers 60, 62 may be used to guide the withdrawal of the leading member 40 (e.g., through the lumen of the deployed vascular device and out the body lumen).

In other cases, however, the operator may be able to provide inputs to the system (e.g., via the user input device 80 of FIG. 4) to select for viewing the image provided by the first ultrasound transducer 60 or the second ultrasound transducer 62. For example, as the operator is advancing the assembly 10, 20 through the body lumen to the target site, the operator may choose to view the images provided via the second transducer 62. Once the assembly 10, 20 has been positioned generally at the target site, the operator may select to view the image provided via the first transducer 60, which may provide a better view of the position (longitudinal and/or rotational) of the vascular device 10 as it is being deployed. Upon completing the deployment of the vascular device 10, the operator may choose to switch back to the image provided via the second transducer 60 to allow the operator to guide the leading member 40 proximally, back through the deployed vascular device 10, and out of the body lumen.

In some embodiments, the vascular device 10 may be configured to have additional features for engaging the target site in different areas of the body lumen. For example, in the depicted embodiment of FIGS. 5-10, the vascular device 10 comprises a main body 100 and at least one branch graft 110 extending from the main body. In FIG. 5, for example, three branch grafts 110 are provided, such as may be configured for engaging the arterial branches in the aortic arch, for example. In this regard, the one or more branch grafts 110 may be configured to be aligned with and extended into corresponding arterial branches. The branch grafts 110 may be formed integrally with the main body 100 in some embodiments, whereas in other embodiments the branch grafts may be formed separately and attached (e.g., stitched, adhered, welded, etc.) to the main body, such that a path for flowing blood is provided through the main body of the vascular device and out through each branch graft into the corresponding arterial branches into which the branch grafts are extended.

In some embodiments, each branch graft 110 may be configured to provide a landing zone for a separate stent graft (not shown) that may be delivered via another delivery device (not shown), through the lumen of the main body 100 of the vascular device 10, and through the supplemental lumen provided by the respective branch graft 110. Accordingly, each branch graft 110 may be configured to extend out from the main body 100 of the vascular device 10 by approximately 0.5 cm to 2 cm so as to provide an adequate landing zone for a supplemental branch graft, as necessary, once deployed within the arterial branch.

To accommodate the branched design of the vascular device 10 shown in FIGS. 5-10 and facilitate accurate positioning and deployment of the vascular device, a delivery device 20 may be provided that is configured to allow for a staged deployment of the vascular device 10 from the delivery device. Accordingly, in some embodiments, the delivery device 20 may comprise an outer sheath 25 having a first lumen 30, as described above, as well as an inner sheath 120 at least partially disposed within the first lumen of the outer sheath and configured to be axially aligned with and movable with respect to the outer sheath. The inner sheath 120 may define a second lumen 125 and a distal end 130, and the second lumen may be configured to receive the vascular device 10 therein.

The inner sheath 120 may, in some embodiments, be configured to radially constrain the main body 100 of the vascular device 10 when the distal end 130 of the inner sheath is disposed proximate the distal end 15 of the vascular device. For example, the inner sheath 120 may be configured to radially constrain the main body 100 of the vascular device 10 when the delivery device 20 is in an delivery configuration (e.g., as shown in FIG. 2, with the leading member 40 engaged with the outer sheath 25), as well as when the outer sheath 25 is moved proximally with respect to the inner sheath 120 and the vascular device 10 to deploy the branch grafts 110 in a first stage of deployment, as shown in FIG. 8.

The outer sheath 25 may be configured to radially constrain both the main body 100 of the vascular device 10, as well as the branch grafts 110 extending therefrom when the outer sheath 25 is in the delivery configuration. As depicted in FIG. 5, for example, in some embodiments, each branch graft 110 may be configured to be disposed between an outer surface of the inner sheath 120 and an inner surface of the outer sheath 25. In this regard, the inner sheath 120 may comprise a slot 135 that is configured to extend around the branch grafts 110, such that the main body 100 of the vascular device 10 is constrained by the inner sheath, while the branch grafts 110 are not constrained.

For example, the slot 135 may include an open end 140 and a closed end 145. The closed end 145 may be disposed at an opposite side of slot 135 than the open end 140, with respect to a long axis of the slot. In the depicted embodiment of FIGS. 5-10, the closed end 145 of the slot 135 is disposed proximally of the open end 140. Thus, the open end 140 may correspond to the distal end 130 of the inner sheath 120, such that the inner sheath is configured to deploy the main body 100 of the vascular device 10 without constraining or interfering with the branch grafts 110.

With reference to FIGS. 6-10, for example, the operator may initially advance towards a target site within the body lumen an assembly comprising a delivery device 20 and a vascular device 10 disposed therein (shown in greater detail in FIGS. 3 and 5, for example). The delivery device may be in a delivery configuration as shown in FIG. 6 and described above and may comprise an outer sheath 25 defining a first lumen. The outer sheath may define a distal end, and the first lumen may be configured to receive the vascular device therein. The delivery device may further comprise a leading member 40 that is configured to be disposed proximate the distal end of the outer sheath and to be engaged with the outer sheath when the delivery device is in a delivery configuration.

In some embodiments, an image of an interior of the patient's blood vessel within which the vascular device is disposed proximate the location of the distal end of the outer sheath 25 may be viewed by an operator of the delivery device. The image may be provided via at least one ultrasound transducer 60 disposed proximate an outer surface of the leading member 40.

With reference to the image, at least one of a longitudinal position or a rotational position of the delivery device may be adjusted. Through such adjustments, the delivery device may be accurately positioned to deploy the vascular device contained therein such that the vascular device and features of the vascular device (e.g., fenestrations 17 shown in FIG. 3 or branch grafts 110) may be aligned with corresponding features of the patient's anatomy to optimize the performance of the vascular device. Once the position of the delivery device is acceptable to the operator, the outer sheath 25 may be moved proximally with respect to the vascular device to deploy the vascular device at the target site.

In some embodiments, the vascular device may comprise a main body 100 and at least one branch graft 110 extending from the main body and configured to be aligned with and extended into an arterial branch at the target site, as shown in FIG. 5 and described above. With respect to FIGS. 7 and 8, moving the outer sheath may include moving the outer sheath 25 to deploy the at least one branch graft 110. With reference to the image, the at least one branch graft 110 may be aligned with an opening of an arterial branch, such that the at least one branch graft extends into the arterial branch. In the depicted embodiment, each of the three branch grafts 110 provided on the vascular device may be aligned with a corresponding arterial branch of the aortic arch, with the operator adjusting the longitudinal and rotational position as necessary with reference to the ultrasound image, as described above, to achieve an accurate position. An inner sheath 120, which may be at least partially disposed within the first lumen of the outer sheath 25 and may surround the main body 100 of the vascular device, may be moved with respect to the outer sheath 25, as shown with reference to FIGS. 8 and 9. In this way, movement of the inner sheath 120 may serve to deploy the main body 100 of the vascular device 10 at the target site, as shown in FIG. 10.

In some cases, the method may further involve moving the leading member 40 proximally through the deployed vascular device 10, back toward the operator, to remove the delivery device from the body lumen. The leading member 40 may be removed, for example, by pulling on the core member 65 of the delivery device, such as via a handle 37 (shown in FIG. 2) of the delivery device that is manipulatable by the operator.

In some embodiments, the at least one ultrasound transducer may be a first ultrasound transducer 60, and the delivery device may further comprise a second ultrasound transducer 62 disposed proximate the outer surface of the leading member 40. Accordingly, a first image provided via the first ultrasound transducer 60 may be viewed, where the first image shows an interior of the first portion of the patient's blood vessel within which the vascular device is disposed adjacent the vascular device, and a second image provided via the second ultrasound transducer 62 may be viewed, where the second image shows an image of an interior of a second portion of the patient's blood vessel within which the vascular device is disposed distally of the leading member. Thus, as described above, images provided via the second ultrasound transducer may be viewed by the operator, for example, to facilitate guidance of the leading member 40, e.g., as engaged with the vascular device and the rest of the delivery device when being advanced to the target site or alone when being removed from the body lumen. The images from the second ultrasound transducer 62 may, as described above, be viewed alongside and/or simultaneously with the images from the first ultrasound transducer 60, or alternatively with the images from the second ultrasound transducer 62.

Embodiments of the delivery device described above and illustrated in the figures may be used to deliver and deploy various types of vascular devices. For example, as described above, a vascular device comprising a simple tubular structure, with fenestrations (as shown in FIG. 3, for example) or without may be delivered via some embodiments of the delivery device. In other examples, a vascular device comprising at least one branch graft may be delivered via some embodiments of the delivery device. In FIG. 5, for example, the vascular device 10 includes three branch grafts 110, such as may be configured for engaging three arterial branches in the aortic arch, for example. In other cases, the vascular device 10 may include two branch grafts, such as may be configured for engaging only two of the arterial branches in the aortic arch or elsewhere in the body lumen.

Other configurations of vascular devices may also be delivered using one or more delivery devices configured according to embodiments of the delivery device described above. With reference to FIGS. 12A and 12B, for example, a vascular assembly may be provided that comprises a first vascular device 11 and a second vascular device 12. One or more of the first and second vascular devices 11, 12 may include one or more branch grafts. For example, the first vascular device 11 in the depicted embodiment includes a single branch graft 111, while the second vascular device 12 includes two branch grafts 112. Although the first and second vascular devices 11, 12 may be separate from each other for purposes of delivery and deployment at the target site, as shown in FIG. 12A, the two components may be configured according to some embodiments to cooperate and act as one device once in position within the body lumen, as illustrated in FIG. 12B. Alternatively, each vascular device 11, 12 may be used independently of the other, such as described above with reference to FIGS. 3 and 5, as in a case where one device is sufficient for addressing the vascular condition of the patient (e.g., only one arterial branch needs to be debranched, in which case only the vascular device 11 having one branch graft 111 in FIG. 12A may be needed).

With reference to FIGS. 12A and 12B, one of the vascular devices (e.g., the device 11 as depicted) may comprise an end 200 that is configured to receive an adjoining end 205 of the other vascular device (e.g., the device 12 as depicted). The receiving end 200 may be configured so as to provide an internal, integral landing zone 210 within the first vascular device 11 for engaging and holding in place the adjoining end 205 of the second vascular device 12, as shown in FIG. 12B. For example, in some embodiments, a portion of the end 200 of the first vascular device 11 may be inverted or folded into the main lumen 215 of the first vascular device so as to create a secondary lumen 220 or space in the vicinity of the branch graft 110. The secondary lumen 220 may be configured (e.g., sized and shaped) to allow blood to flow from the main lumen 215 to the branch graft 110 and into the debranched arteries, while at the same time providing a landing zone of suitable length within the first vascular device 11 for engaging the second vascular device 12, where the landing zone would not have existed otherwise due to the presence of the branch graft 111. Other configurations for a two-component vascular assembly are described in U.S. application Ser. No. 13/651,920, titled "Method and Apparatus for Endovascular Therapy of Aortic Pathology," the contents of which are incorporated herein by reference.

Thus, according to embodiments of the invention described above, embodiments of the delivery device may be used to deliver each vascular device 11, 12 to the target site, as described with respect to the devices depicted in FIGS. 2-11. For example, in a case in which only one vascular device 11 is needed (e.g., to address a portion of the aortic arch including only the innominate artery 345, shown in FIG. 1), a delivery device 20 such as described above may be used to deliver the vascular device 11 to the target site. In a case in which two vascular devices 11, 12 are needed to address all three branch arteries of the aortic arch, for example, a first delivery device 20 may be used according to the embodiments described above to deliver the first vascular device 11, and a second delivery device 20 may be used according to the embodiments described above to deliver the second vascular device 12 and engage the second vascular device 12 with the first vascular device 11 (e.g., as shown in FIG. 12B). The two devices 11, 12 may be delivered and installed during the same procedure, or, in some cases, one of the devices may be delivered and installed during a subsequent procedure, such as in cases in which the patient's vascular condition deteriorates and the need to address additional branch arteries arises.

In addition to differences in the particular configurations of the vascular devices 10, 11, 12 or delivery devices 20, the materials used for the delivery device and/or the vascular device may also vary and may be selected based on the particular application (e.g., the particular target site within the body lumen to be addressed), the design of the devices, and/or the operator's preferences. For example, some components of the delivery device, such as the outer sheath 25, the inner sheath 120 and/or the leading member 40, may be made of polymer material or other biocompatible material, as an example, whereas other components, such as the core member 65, external handles (e.g., handle 37 shown in FIG. 2), etc. may be made of metal (e.g., stainless steel or titanium), polymer material, or other biocompatible material.

At least some portions of the vascular device 10 may, in some embodiments, comprise a shape memory alloy such as nitinol and may be configured to move between a contracted configuration when received within and radially constrained by the delivery device (e.g., the outer sheath 25 and/or the inner sheath 120) and an expanded configuration when deployed from the delivery device, as described above. Other components of the vascular device 10, such as some portions of the main body 100 and/or the branch grafts 110, may be made of a fabric (e.g., Gore-tex® or Dacron® fabric webbing) and/or may comprise or be used in combination with a shape memory alloy such as nitinol. In still other embodiments, portions of the vascular device may be expanded by the operator, such as via balloon expansion or other expansion mechanisms.

Moreover, in some embodiments, the inner sheath 120 of the delivery device 20 may have different configurations to allow the branch grafts 110 to be deployed from the outer sheath 25, while at the same time continuing to constrain the main body 100. For example, the inner sheath may comprise a polymer mesh, and the polymer may be hydrophilic. In some embodiments, the inner sheath 120 may be a thin material in comparison to, for example, the outer sheath 25, such that it resembles a skin layer that surrounds portions of the vascular device, as shown in FIG. 5.

In addition to the embodiments described above, e.g., with respect to FIGS. 5-9, in some cases the inner sheath 120 may comprise a spiral structure, rather than a slotted tubular structure. For example, with reference to FIG. 13, in some embodiments a coil 121 may be provided to surround and constrain the main body 100 of the vascular device 10. The coil 121 may be configured to spirally wrap around the main body 100, such that the branch grafts 110 are disposed between adjacent loops of the coil and are not themselves constrained by the coil.

The coil 121 that serves as the inner sheath in the embodiment of FIG. 13 may, in some cases, be configured to slidably engage corresponding grooves 122 defined on an inner surface 26 of the outer sheath 25, shown in FIG. 14. Thus, an operator may move the outer sheath proximally (in the direction D shown in FIG. 13) with respect to the inner sheath (e.g., the coil 121) in such embodiments by rotating the outer sheath in the direction T shown in FIG. 13. As the outer sheath 25 is moved proximally (via rotation), the branch grafts 110 of the vascular device 10 may be deployed (e.g., extended outwardly from the main body 100), as shown. In this example, the main body 100 of the vascular device 10 may be deployed by moving the inner sheath in the form of the coil 121 proximally with respect to the vascular device 10, such as by rotating the coil in the direction T while holding the rotational position of the outer sheath 25 is held steady. In this way, the coil 121 may slide along the grooves 122 of the outer sheath (FIG. 14) and may gradually be moved off the main body 100 in the direction D, thereby allowing the main body to be expanded to fully deploy the vascular device 10. Embodiments of the inner sheath, when provided as a coil 121 or otherwise, may further be configured such that the main body may be able to be recaptured by the inner sheath and/or the outer sheath, such as to allow for further repositioning of the distal end of the delivery device 20 prior to deployment of the vascular device 10 at the target site.

As noted above, embodiments of the delivery devices and vascular devices described above may be delivered to a target site in the patient's body using various methods, such as over a guidewire, e.g., using the Seldinger technique. The particular procedure may depend on the location of the target site, the condition of the patient's vasculature, the operator's preferences, and other considerations. In some cases, for example, wire access may be gained via the femoral artery and/or via the right brachial artery or the subclavian/axillary artery, and the delivery (or stages of the delivery, such as when multiple delivery devices and/or vascular devices are involved) may be accomplished in a retrograde and/or an antegrade fashion.

In some cases, the vascular device may be pre-packaged within a delivery device for use in a medical procedure. For example, an operator may receive (e.g., from the manufacturer) a delivery device according to one or more of the embodiments described above, where the delivery device includes a vascular device already disposed therein, ready for use. The pre-packaged delivery device and vascular device may be contained in a sterile solution, e.g., water or saline, such that upon insertion and positioning of the appropriate guidewire(s) within the patient's vasculature, the delivery device with the vascular device therein may be positioned over the guidewire and advanced to the target site.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. In some embodiments, certain ones of the procedures or methods above may be modified or further amplified as described below.

For example, although the description herein uses the example of vascular devices that are configured to be delivered intravascularly for treatment of a target site in the aortic arch (e.g., in the area of the innominate artery, the left common carotid artery, and the left subclavian artery), conditions in other areas of the aorta may also be addressed using embodiments of the delivery device and vascular assembly described above. For example, with reference to FIG. 1, pathologies of the visceral aorta in the area of the celiac artery, SMA, and renal arteries may also be treated using similar devices and procedures.

Modifications, additions, or amplifications to the operations above may be performed in any order and in any combination. For example, although the methods described above and in the related figures discuss positioning of the vascular device and or components of the vascular device in a certain order, in some cases a second component may be positioned at the target site prior to placement of a first component.

Also, the delivery devices and vascular devices, in some cases, may include more or fewer features than those described herein. For example, additional fenestrations and/or branch grafts may be included, depending on the configuration of the arterial branches in the area to be treated and/or the anatomy of the particular patient to be treated. With respect to the delivery device, the depicted embodiments show a delivery device having two ultrasound transducers disposed thereon, as described above. It is understood, however, that in some embodiments the delivery device may include only the first ultrasound transducer or only the second ultrasound transducer. In still other embodiments, more than two ultrasound transducers may be provided. For example, multiple ultrasound transducers (e.g., 2, 3, 4, or more) may be provided about a circumference of the leading member of the delivery device to provide a full range of view (e.g., approximately 360°) proximate the distal end of the delivery device and/or vascular device, as necessary. Although specific terms are employed herein, they are used in a generic and descriptive sense only and not for purposes of limitation.

What is claimed is:

1. A method for using real-time feedback to position a vascular device proximate a target site within a body lumen comprising:

advancing toward a target site within the body lumen an assembly comprising a delivery device with a vascular device disposed therein, wherein the vascular device comprises a main body and at least one branch graft configured to be aligned with and extended from the main body into an arterial branch, and wherein the delivery device is in a delivery configuration and comprises:

an outer sheath defining a first lumen, wherein the outer sheath defines a distal end thereof;

an inner sheath defining a second lumen, wherein the inner sheath is at least partially disposed within the first lumen of the outer sheath, and wherein the second lumen at least partially receives the main body of the vascular device therein; and a leading member configured to be disposed proximate the distal end of the outer sheath and to be engaged with the outer sheath when the delivery device is in the delivery configuration;

viewing a first image provided via a first ultrasound transducer, wherein the first image shows an interior of a first portion of the patient's blood vessel within which the vascular device is disposed adjacent the vascular device, and wherein the first ultrasound transducer is disposed proximate the distal end of the outer sheath;

adjusting at least one of a longitudinal position or a rotational position of the delivery device with reference to the first image;

separating the leading member from the outer sheath;

moving the outer sheath proximally with respect to the vascular device to deploy the vascular device at the target site; and viewing a second image provided via a second ultrasound transducer, wherein the second image shows an image of an interior of a second portion of the patient's blood vessel within which the vascular device is disposed distally of the leading member, and wherein the second ultrasound transducer is disposed proximate a distal tip of the leading member, wherein the inner sheath radially constrains the main body of the vascular device while the at least one branch graft deploys through an opening in the inner sheath.

2. The method of claim 1 further comprising:
aligning the at least one branch graft with an opening of an arterial branch, such that the at least one branch graft extends into the arterial branch with reference to the first image, and moving the inner sheath with respect to the outer sheath, to deploy the main body of the vascular device.

3. The method of claim 1 further comprising moving the leading member proximally through the deployed vascular device to remove the delivery device from the body lumen.

4. The method of claim 1, wherein the target site is in the aortic arch.

5. The method of claim 4, wherein the target site is one of the innominate artery, the left common aortic artery, or the left subclavian artery.

6. The method of claim 1, wherein the target site is in the visceral aorta.

7. The method of claim 6, wherein the target site is one of the celiac artery, superior mesenteric artery, or renal artery.

8. The method of claim 1, wherein the first image and second image are real-time images.

* * * * *